(12) United States Patent
Jing

(10) Patent No.: US 10,859,561 B2
(45) Date of Patent: Dec. 8, 2020

(54) PROTEOLIPOSOME AND PRODUCTION METHOD THEREOF

(71) Applicant: Purdue Research Foundation, West Lafayette, IN (US)

(72) Inventor: Peng Jing, Fort Wayne, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/136,911

(22) Filed: Sep. 20, 2018

(65) Prior Publication Data

US 2019/0017990 A1 Jan. 17, 2019

Related U.S. Application Data

(62) Division of application No. 15/399,061, filed on Jan. 5, 2017, now Pat. No. 10,107,791.

(60) Provisional application No. 62/274,815, filed on Jan. 5, 2016.

(51) Int. Cl.
| | | |
|---|---|---|
| *A61K 38/00* | (2006.01) | |
| *G01N 33/487* | (2006.01) | |
| *C07K 14/005* | (2006.01) | |
| *B82Y 15/00* | (2011.01) | |
| *B82Y 5/00* | (2011.01) | |

(52) U.S. Cl.
CPC ..... *G01N 33/48721* (2013.01); *C07K 14/005* (2013.01); *B82Y 5/00* (2013.01); *B82Y 15/00* (2013.01); *C07K 2319/21* (2013.01); *C12N 2795/10222* (2013.01)

(58) Field of Classification Search
None
See application file for complete search history.

(56) References Cited

U.S. PATENT DOCUMENTS

2008/0218184 A1* 9/2008 White .............. G01N 33/48721
324/693

* cited by examiner

*Primary Examiner* — Jeanette M Lieb
(74) *Attorney, Agent, or Firm* — Purdue Research Foundation; Liang Zeng Yan

(57) ABSTRACT

The invention discloses a proteoliposome or a planar lipid bilayer membrane comprising a single protein manufactured using glycerol or polyethylene glycols (PEG) in the rehydration step. Products so prepared are useful for nanopore sensing technology, including ultrafast DNA sequencing and biomedical diagnostic applications.

9 Claims, 12 Drawing Sheets

100 μm

PROTEOLIPOSOME AND PRODUCTION METHOD THEREOF

CROSS-REFERENCE TO RELATED APPLICATIONS

This present U.S. patent application is a divisional of U.S. non-provisional patent application 15/399,061, filed on Jan. 5, 2017, which claims the benefit of the U.S. Provisional Patent Application No. 62/274,815, filed on Jan. 5, 2016, the content of which is incorporated herein expressly by reference in its entirety into this present application.

TECHNICAL FIELD

The present disclosure generally relates to liposome preparation, and in particular to a proteoliposome or a planar lipid bilayer membrane comprising a single protein manufactured using glycerol or polyethylene glycols (PEG) in the rehydration step. Products so prepared are useful for nanopore sensing technology, including ultrafast DNA sequencing and biomedical diagnostic applications.

BACKGROUND

This section introduces embodiments that may help facilitate a better understanding of the disclosure. Accordingly, these statements are to be read in this light and are not to be understood as admissions about what is or is not prior art.

Liposomes are small artificial vesicles of spherical shape having one or more phospholipid bilayers. Due to their size and hydrophobic and hydrophilic character (besides biocompatibility), liposomes are promising systems for drug delivery, nanopore sensing platform technology and other vast applications in modern biotechnologies. Liposome properties differ considerably with lipid composition, surface charge, size, and the method of preparation.

A proteoliposome is a liposome into which one or more proteins have been inserted, wherein the protein maintains its biological functions (M. Scalise, et al., *Pharmaceutics* 2013, 5, 472-497). Those inserted proteins, including membrane transporter proteins, viral portal proteins, and other hydrophobic transmembrane channel proteins, can be structurally and functionally investigated.

A viral portal protein is a protein embedded in the capsid shell in bacteriophages, which serves as a conduit for single stranded DNA, single stranded RNA or double stranded DNA to pass through. A membrane channel protein, or a protein channel, is a protein that enables the transport of specific substances across a cell membrane. Protein channels are a traffic system in a cell that allows the transportation of water, chemicals and electric signals across the cell membrane. They affect the function of the cell by controlling the traffic of the materials and signals. More specialized protein channels transport calcium, sodium and other ions to change the electrical potential across cell membranes causing the cells to react to stimuli. A proteoliposome with integrated membrane channel proteins is an ideal man-made system to study those biological processes of living cells. Furthermore, a proteoliposome with a single portal protein molecule could fuse quickly and efficiently to a planar lipid bilayer for diverse nanopore sensing applications.

The planar lipid bilayer technology is a technique that yields incredibly useful structural-functional information about a single channel protein. It is also currently actively utilized as a powerful platform using biological protein nanopore for the development of single-molecule nanopore sensing technology, as well as ultrafast DNA sequencing technology. Portal protein GP10 from the bacteriophage $^{SM}29$ was the first phage portal protein shown to be successfully inserted into planar bilayer membranes, thereby it may inspire more researchers to apply the techniques to portal proteins from the other bacteriophages (D. Wendell, et al., *Nat Nanotechnol*, 2009, 4, 765-772). More recently, the technique has been further explored as a single-molecule sensing platform for the development of nanopore sensors (W. Li, et al., *Angew Chem Int Ed Engl*, 2013, 52, 4350-4355; S. Majd, et al., *Current Opinion in Biotechnology*, 2010, 21, 439-476) and ultrafast DNA sequencing technology (H. Bayley, *Phys Life Rev*, 2012, 9, 161-163; discussion 174-166; M. Wanunu, *Phys Life Rev*, 2012, 9, 125-158).

However, insertion of a channel protein into planar bilayer membrane is technically difficult as well as time-consuming. Before the fusion of phage portal protein into the planar bilayer membrane, the portal protein is first reconstituted and incorporated in proteoliposomes. Most of the phage portal proteins have low solubility, and may self-aggregate during the preparation of the proteoliposomes. Furthermore, the fusion of the formed proteoliposomes to the planar bilayer membrane is sporadic, unpredictable and varied significantly from experiment to experiment. Due to the lack of experimental consistency between laboratories, the results from different methodologies reported for generating fusible proteoliposomes are highly variable. To enable wide and practical uses of the planar lipid bilayer and the single-molecule nanopore sensing technologies, there are unmet needs for a simple, practical, and economically viable preparation of proteoliposomes, which could be effectively and efficiently fused into a planar lipid bilayer.

BRIEF SUMMARY OF INVENTION

In one aspect, this invention discloses a new method to prepare a proteoliposome, wherein the method provides several significant improvements over the conventional dehydration-rehydration process. The new method renders a surprising and unexpected improvement in stabilizing the hydrophobic proteins. The method replaces sucrose and expensive surfactants traditionally used in the process of liposome preparation with glycerol or polyethylene glycols (PEG). The added glycerol or PEG solubilizes those hydrophobic proteins while preventing them from aggregation and/or precipitation.

In another aspect, the invention disclosed herein is related to a proteoliposome incorporating a membrane-bound protein, portal protein, or another hydrophobic channel membrane protein. The new method renders a surprising and unexpected improvement in stabilizing those hydrophobic proteins.

Yet in another aspect, the introduction of glycerol in the preparation of the liposomes makes it possible to adjust the density and osmotic pressure of the proteoliposomes prepared thereof by varying the concentration of glycerol in the rehydration step. The adjusted density and osmotic pressure of the proteoliposomes so prepared control the interaction of the proteoliposomes with a planar bilayer membrane and the subsequent fusion of the proteoliposome into the planar bilayer membrane. The proteoliposomes so prepared provide a much fast insertion of a phage portal protein into a planar bilayer membrane. With the method disclosed in this invention, the insertion of a portal protein into a planar bilayer membrane could be accomplished in less than one minute, as compared with more than eight minutes using a conventional process. The planar lipid bilayer with a fused portal protein may find applications in nanopore DNA sequencing, drug delivery, and nanopore sensing technology.

In another aspect, the proteoliposomes prepared by the method disclosed in this invention have demonstrated an exceptional stability and a much improved shelf-life, which makes storage and transport of those proteoliposomes more convenient and therefore an economically viable commercial product. The proteoliposomes so prepared can be commercialized for different biomedical research and commercial applications, e.g., liposome-based drug delivery system, nanopore sensing technologies, ultrafast DNA sequencing, and others.

In another aspect, the method disclosed in this invention eliminates the highly expensive surfactants, which was an essential component in the traditional method for proteoliposome preparation in research and commercial settings. Therefore the method disclosed in this invention will provide a much profitable product because glycerol is a low-priced, mass industrial byproduct.

Yet in another aspect, the method disclosed in this invention can be used for a wide variety of phage viral portal proteins, hydrophobic membrane channel proteins, hydrophobic membrane-bound proteins, and others. This method will significantly expand the potential applications of this platform technology in single-molecule nanopore sensing, ultrafast DNA sequencing, and other biomedical research and commercial applications.

In another aspect, the method disclosed in this invention may be of practical applications in performing in-vitro real-time structural functional studies on the roles that portal proteins play in the viral assembly, DNA packaging, and DNA ejection among a variety of the tailed bacteriophages and herpesviruses.

In one aspect, the current invention discloses a method for the preparation of proteoliposomes reconstituted with a membrane-bound channel protein, a viral portal protein, or other hydrophobic membrane channel proteins, the method comprising:
a) preparing a lipid solution in an organic solvent;
b) preparing a protein solution;
c) combining said lipid solution and said protein solution in a flask;
d) removing said organic solvent from the combined solution from step c), under vacuum with constant mixing, to afford a residue;
e) adding an aqueous buffer to the residue of step d), wherein said aqueous buffer is doped with glycerol;
f) rehydrating the mixture of step e) by gentle agitation;
g) extruding the rehydrated mixture of step f) through a polycarbonate membrane, wherein the polycarbonate membrane has a pore size ranging from about 50 nm to about 400 nm; and
h) repeating step g) for about five to fifty times to afford a proteoliposome product.

In one aspect, the current invention discloses a method for the preparation of proteoliposomes using glycerol, wherein the glycerol concentration may range from about 1% to about 99% (v/v).

In another aspect, this invention discloses a method for preparation of a proteoliposome, the method comprising:
a) preparing a lipid solution in an organic solvent;
b) preparing a protein solution;
c) combining said lipid solution and said protein solution in a flask;
d) removing said organic solvent from the combined solution from step c), under vacuum with constant mixing, to afford a residue;
e) adding an aqueous buffer to the residue of step d), wherein said aqueous buffer is doped with polyethylene glycols (PEG);
f) rehydrating the mixture of step e) by gentle agitation;
g) extruding the rehydrated mixture of step f) through a polycarbonate membrane, wherein the polycarbonate membrane has a pore size ranging from about 50 nm to about 400 nm; and
h) repeating step g) for about five to fifty times to afford a proteoliposome product.

In one aspect, the current invention discloses a method for the preparation of proteoliposomes using PEG, wherein the concentration of said PEG may range from about 0.1% to 60% (v/v).

In another aspect, the current invention discloses a method for the preparation of a proteoliposome using PEG, wherein the molecular weight of said PEG may range from about 200 Da to 8,000 Da.

In another aspect, this invention uses a lipid in the preparation of a proteoliposome, wherein said lipid may be 1,2-diphytanoyl-sn-glycero-3 phosphocholine (DPhPC), diacetyl phosphatidylcholine (DAcPC), 1,2-dioleoyl-sn-glycero-3-phosphocholine (DOPC), or another compatible lipid.

In another aspect, this invention discloses a method for the preparation of a proteoliposome containing a functional protein, wherein said functional protein may be a channel protein, a membrane-bound protein, a viral portal protein, or another hydrophobic transmembrane protein.

In another aspect, the current invention is related to a proteoliposome prepared by the method disclosed herein, wherein the proteoliposome incorporates a channel protein, a membrane-bound protein, a viral portal protein, or another hydrophobic membrane protein.

In another aspect, the current invention is related to a proteoliposome prepared by the method disclosed herein, wherein the proteoliposome incorporates a mutant portal protein C-His GP10 from bacteriophage Phi29, a mutant portal protein GP20 (20amN50(Q325am)) from bacteriophage T4, hemolysin, or MspA porin.

In an illustrative aspect, this invention is related to a planar lipid bilayer membrane fused with a single channel protein, wherein said channel protein is derived from a proteoliposome prepared by a method disclosed herein.

In another aspect, the method disclosed in this invention uses an aqueous buffer in the preparation of a proteoliposome, wherein the buffer may be 2-(4-(2-hydroxyethyl)-1-piperazinyl) ethane sulfonic acid (HEPES), phosphate, or Tris buffer with a pH value ranging from about 3 to about 10.

BRIEF DESCRIPTION OF THE FIGURES

The above and other objects, features, and advantages of the present invention will become more apparent when taken in conjunction with the following description and drawings wherein identical reference numerals have been used, where possible, to designate identical features that are common to the figures, and wherein.

DETAILED DESCRIPTION

Figure 1A:
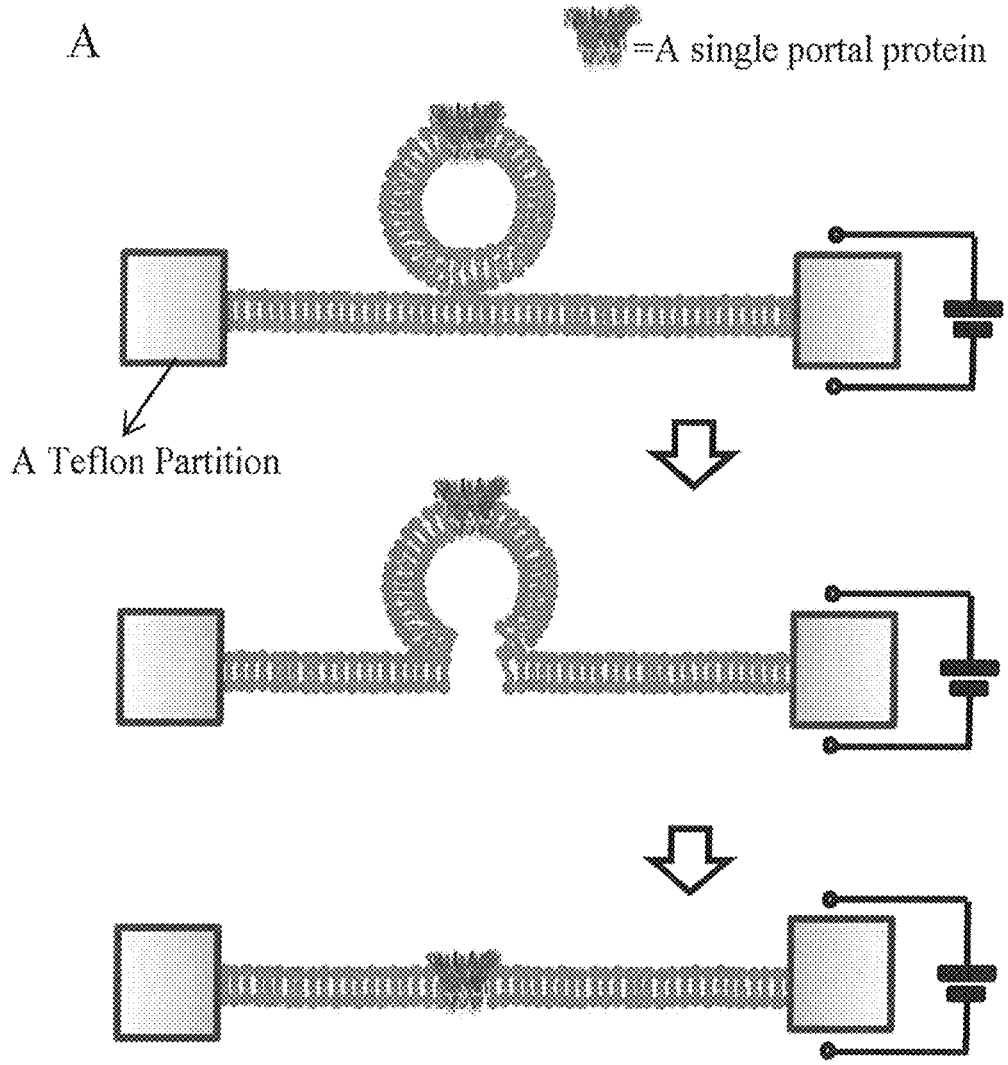
FIG. 1A is a schematic for the process of a single proteoliposome fused into a planar lipid bilayer membrane.

For the purposes of promoting an understanding of the principles of the present disclosure, reference will now be made to the embodiments illustrated in the drawings, and specific language will be used to describe the same. It will nevertheless be understood that no limitation of the scope of this disclosure is hereby intended.

As used herein, the following terms and phrases shall have the meanings set forth below. Unless defined otherwise, all technical and scientific terms used herein have the same meaning as commonly understood to one of ordinary skilled in the art.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range. Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "substantially" as used herein refers to a majority of, or mostly, as in at least about 60%, 70%, 80%, 90%, 95%, 96%, 97%, 98%, 99%, 99.5%, 99.9%, or at least about 99.99% or more.

A liposome is an assembly of biologically functional molecules and is formed by dispersing and re-associating a lipid, which is a biomembrane-constituting molecule, in an aqueous solution and has a structure like a cellular membrane. The application of liposome is under investigation as applied to biomedical diagnosis, targeted drug delivery, biological therapeutics, vaccine delivery, and other various industrial fields.

Proteoliposomes are liposomes incorporated with functional protein molecules. For the purpose of single-molecule nanopore sensing technology, the size of the proteoliposome as disclosed in this invention is in the range of nanometers and each proteoliposome is preferably incorporated with one single channel protein molecule, such as a viral portal protein molecule, or other membrane channel proteins. The proteoliposome with a single portal protein molecule could fuse quickly and efficiently to a planar lipid bilayer for diverse nanopore sensing applications.

The lipid to be used in the preparation of proteoliposome may be any of those generally used for the production of liposome, and examples thereof may include 1,2-diphytanoyl-sn-glycero-3 phosphocholine (DPhPC), diacetyl phosphatidylcholine (DAcPC), 1,2-dioleoyl-sn-glycero-3-phosphocholine (DOPC), distearoylphosphatidylcholine, 1-palmitoyl-2-oleoyl-sn-glycero-3-phosphocholine (POPC), and the alike. These lipids may be used singly or in combination of two or more kinds thereof.

In one illustrative embodiment, this invention discloses a new method to prepare a proteoliposome, wherein the method provides several significant improvements over the conventional dehydration-rehydration process. The new method renders a surprising and unexpected improvement in stabilizing the hydrophobic proteins. The method replaces sucrose and expensive surfactants traditionally used in the process of liposome preparation with glycerol or polyethylene glycols (PEG). The added glycerol or PEG solubilizes those hydrophobic proteins while preventing them from aggregation and/or precipitation.

In another illustrative embodiment, the invention disclosed herein is related to a proteoliposome incorporating a membrane-bound protein, portal protein, or another hydrophobic channel membrane protein.

Yet in another illustrative embodiment, the introduction of glycerol in the preparation of the liposomes makes it possible to adjust the density and osmotic pressure of the proteoliposomes prepared thereof by varying the concentration of glycerol in the rehydration step. The adjusted density and osmotic pressure of the proteoliposomes so prepared control the interaction of the proteoliposomes with a planar bilayer membrane and the subsequent fusion of the proteoliposome into the planar bilayer membrane. The proteoliposomes so prepared provide a much fast insertion of a phage portal protein into a planar bilayer membrane. With the method disclosed in this invention, the insertion of a portal protein into a planar bilayer membrane could be accomplished in less than one minute, as compared with more than eight minutes using a conventional process. The planar lipid bilayer with a fused portal protein may find applications in nanopore DNA sequencing, drug delivery, and nanopore sensing technology.

In another illustrative embodiment, the proteoliposomes prepared by the method disclosed in this invention have demonstrated an exceptional stability and a much improved shelf-life, which makes storage and transport of those proteoliposomes more convenient and therefore an economically viable commercial product. The proteoliposomes so prepared can be commercialized for different biomedical research and commercial applications, e.g., liposome-based drug delivery system, nanopore sensing technologies, ultrafast DNA sequencing, etc.

In another illustrative embodiment, the method disclosed in this invention eliminates the highly expensive surfactants, which was an essential component in the traditional method for proteoliposome preparation in research and commercial settings. Therefore the method disclosed in this invention will provide a much profitable product because glycerol is a low-priced, mass industrial byproduct.

Yet in another illustrative embodiment, the method disclosed in this invention can be used for a wide variety of bacterial phage portal proteins, hydrophobic channel proteins, hydrophobic membrane-bound proteins, and others. This method will significantly expand the potential applications of this platform technology in single-molecule nanopore sensing, ultrafast DNA sequencing, and other biomedical research and commercial applications.

In another embodiment, the method disclosed in this invention may be of practical application in performing in-vitro real-time structural functional studies on the roles that portal proteins play in the head assembly, DNA packaging, and DNA ejection among a variety of the tailed bacteriophages and herpesviruses.

In one illustrative embodiment, the current invention discloses a method for the preparation of proteoliposomes reconstituted with a membrane-bound channel protein, a bacterial or viral portal protein, or other hydrophobic membrane proteins, the method comprising:
    a) preparing a lipid solution in an organic solvent;
    b) preparing a protein solution;
    c) combining said lipid solution and said protein solution in a flask;
    d) removing said organic solvent from the combined solution from step c), under vacuum with constant mixing, to afford a residue;
    e) adding an aqueous buffer to the residue of step d), wherein said aqueous buffer is doped with glycerol;
    f) rehydrating the mixture of step e) by gentle agitation;
    g) extruding the rehydrated mixture of step f) through a polycarbonate membrane, wherein the polycarbonate membrane has a pore size ranging from about 50 nm to about 400 nm; and
    h) repeating step g) for about five to fifty times to afford a proteoliposome product.

In one illustrative embodiment, the current invention discloses a method for the preparation of proteoliposomes using glycerol in the step of rehydration, wherein the glycerol concentration may range from about 1% to about 99% (v/v).

In a preferred embodiment, the current invention discloses a method for the preparation of proteoliposomes using glycerol in the step of rehydration, wherein the glycerol concentration may range from about 20% to about 35% (v/v).

In one illustrative embodiment, the current invention discloses a method for the preparation of proteoliposomes containing a functional protein, wherein said functional protein is a bacterial or viral portal protein, a channel protein, or another membrane protein.

In another illustrative embodiment, the current invention discloses a method for the preparation of proteoliposomes containing a mutant portal protein C-His GP10 from bacteriophage Phi29, a mutant portal protein GP20 (20amN50 (Q325am)) from bacteriophage T4, hemolysin, MspA porin, or the like.

In another illustrative embodiment, this invention discloses a method for preparation of a proteoliposome, the method comprising:
    a) preparing a lipid solution in an organic solvent;
    b) preparing a protein solution;
    c) combining said lipid solution and said protein solution in a flask;
    d) removing said organic solvent from the combined solution from step c), under vacuum with constant mixing, to afford a residue;
    e) adding an aqueous buffer to the residue of step d), wherein said aqueous buffer is doped with polyethylene glycols (PEG);
    f) rehydrating the mixture of step e) by gentle agitation;
    g) extruding the rehydrated mixture of step f) through a polycarbonate membrane, wherein the polycarbonate membrane has a pore size ranging from about 50 nm to about 400 nm; and
    h) repeating step g) for about five to fifty times to afford a proteoliposome product.

In one aspect, the current invention discloses a method for the preparation of proteoliposomes using PEG in the step of rehydration, wherein the concentration of said PEG may range from about 0.1% to 60% (v/v).

In a preferred embodiment, the current invention discloses a method for the preparation of proteoliposomes using PEG in the step of rehydration, wherein the PEG concentration may range from about 2% to about 30% (v/v).

In another aspect, the current invention discloses a method for the preparation of proteoliposomes using PEG, wherein the molecular weight of said PEG may range from about 200 Da to 8,000 Da.

In another aspect, this invention uses a lipid in the preparation of a proteoliposome, wherein said lipid may be 1,2-diphytanoyl-sn-glycero-3 phosphocholine (DPhPC), diacetyl phosphatidylcholine (DAcPC), 1,2-dioleoyl-sn-glycero-3-phosphocholine (DOPC), or another compatible lipid.

In another aspect, this invention is related to a method for the preparation of a proteoliposome containing a functional protein, wherein said protein may be a channel protein, a membrane-bound protein, a viral portal protein, or another hydrophobic membrane protein.

In another aspect, the current invention is related to a proteoliposome prepared by a method disclosed herein, wherein the proteoliposome incorporates a channel protein, a membrane-bound protein, a bacterial or viral portal protein, or another hydrophobic membrane protein.

In another aspect, the current invention is related to a proteoliposome prepared by the method disclosed herein, wherein the proteoliposome incorporates a mutant portal protein C-His GP10 from bacteriophage Phi29, a mutant portal protein GP20 (20amN50(Q325am)) from bacteriophage T4, hemolysin, or MspA porin.

In another aspect, the method disclosed in this invention uses an aqueous buffer in the preparation of a proteoliposome, wherein the buffer may be 2-(4-(2-hydroxyethyl)-1-piperazinyl) ethane sulfonic acid (HEPES), phosphate, or Tris buffer with a pH value ranging from about 3 to about 10.

In an illustrative embodiment, this invention is related to a planar lipid bilayer membrane fused with a single channel protein, wherein said channel protein is derived from the proteoliposome prepared by a method disclosed herein.

The present invention may be better understood in light of the following non-limiting methods and examples.

Expression and Purification of C-His GP10 Connectors

The gene of C-His GP10 is from a constructed plasmid pET-21a (+) C-GP 10. After the plasmid is transformed into BL21 (DE3) cells (EMD Millipore, Billerica, Mass.), the C-His GP10 protein is overexpressed by the transformed cells cultured in an LB medium containing 50 μg/mL Ampicillin (Sigma Pharmaceutical, Rowville, Australia). Isopropyl-β-D-thio-galactoside (IPTG) (Sigma Pharmaceutical, Rowville, Australia) is used to induce the protein expression. The bacterial cells are harvested by centrifugation and re-suspended in 50 mM $NaH_2PO_4$ 500 mM NaCl, 10 mM imidazole (pH 7.4) with 15% glycerol and subsequently disrupted by passage of the mixture through a French press. The supernatant is collected by centrifugation at a speed of 16000 rpm for 20 min. C-His GP10 is purified using a column filled with a HisPur Ni-NTA Resin (Cat #88221, Thermo Scientific, Waltham, Mass.). The column is washed with 50 mM $NaH_2PO_4$ 500 mM NaCl, 50 mM imidazole (pH 7.4) with 15% glycerol. Elution of the target protein is carried out with a buffer containing 50 mM NaH2PO4 500 mM NaCl, 0.5 M imidazole (pH 7.4), and 15% glycerol. Concentrations of the protein are determined using a Coomassie (Bradford) Protein Assay Kit (Cat #23220 Thermo Scientific, Waltham, Mass.).

Preparation of Proteoliposomes Reconstituted with Portal Proteins

For comparison, two methods are used to prepare C-His GP10 reconstituted proteoliposomes. The new method disclosed herein is defined as Experimental Method hereafter. The conventional method previously reported is defined hereafter as Conventional Method (D. Wendell, et al., Nat. Nanotechnol., 2009, 4, 765-772). Briefly, a lipid stock solution of DPhPC in chloroform or methylene chloride is added to a round-bottom flask. The organic solvent chloroform or methylene chloride was evaporated to form a lipid film under vacuum using a rotavapor. A solution of purified protein C-His GP10 is then added to the conducting buffers with 200 mM sucrose and used to rehydrate the lipid film to form a suspension solution of multi-laminar liposomes for a further membrane extrusion.

For the new method disclosed in this invention, the lipid stock solution of DPhPC in chloroform is premixed with a purified portal protein containing 15% (V/V) glycerol (the volume ratio of chloroform vs. the aqueous solution is 4:1). The resultant mixture solution is subsequently added to a round-bottom flask. In the round-bottom flask, two clear phases, oil phase and water phase, can be visualized and no aggregation can be found in either phase. Applying a vacuum for 10 min while the flask is rotating on a rotavapor, the solvent chloroform is completely evaporated which resulted in the formation of a viscous gel. The gel is then rehydrated by adding a buffer solution containing 15-30% glycerol (V/V), which results multi-laminar liposomes. For ease of comparison of the two methods, a final molar ratio of the lipid vs C-His GP10 connector protein was kept at 600:1 for both methods.

To prepare unilaminar liposomes, an extrusion method is used to further process the suspension of multilaminar vesicles. After passing the multilaminar vesicle suspension solution through a 400 nm polycarbonate membrane for about twenty times using the mini extruder (Avanti Polar Lipids, Alabaster, Ala.), unilaminar proteoliposomes are obtained, which are stored as aliquots at −80° C. for long-term use and stability evaluation.

Insertion of the Portal Proteins into a Planar Bilayer Membrane

A horizontal bilayer chamber, abbreviated as BLM chamber, (BCH-1A, Eastern Scientific, Rockville, Md.) with an LED light below to optically monitor the position of the aperture on a Teflon partition is used for all planar lipid bilayer experiments. The BLM chamber has two separated compartments, cis- and trans-, by the Teflon partition (200 μm TP-02, Eastern Scientific, Rockville, Md.). Both compartments are filled with a conducting buffer, 5 mM Tris buffer (pH 8.0) with 1 M NaCl if not otherwise specified. Liposomes reconstituted with proteins are added to the cis-compartment. As a comparison, a vertical version of BLM chamber has also been used for the vesicle insertion experiments. A planar lipid bilayer is formed across a 200-μm aperture in the wall of a Delrin cup (BCH-13A, Warner Instruments; Hamden, Conn.) with a working volume of 1 mL in the chamber.

To form a bilayer membrane, the aperture of the Teflon partition is pre-painted and air-dried with 0.5 μL 3% (w/v) DPhPC in an n-decane solution three times before the buffer is added. The planar bilayer is formed by depositing a 10 mg/mL of DPhPC n-decane solution over the aperture in the buffer. The process for the formation of bilayer membrane on the aperture is monitored by measuring the current response under triangular voltage stimulation since the amplitude of the resulting square wave current response is proportional to the value of bilayer capacitance. The membrane capacitance threshold range is set to be from 80 to 100 pF. Liposomes are introduced to the chamber only after the capacitance value reaches the threshold range of 80 to 100 pF. The amount of the proteoliposomes introduced is set to be 1 μL of the stock liposome solution.

Channel Conductance Analysis

The channel conductance is measured through a pair of Ag/AgCl electrodes connected to a BLM setup. The BLM setup includes a patch-clamp amplifier with a bilayer headstage (BC-535, Warner Instruments; Hamden, Conn.), an in-house made Farady cage placed on a vibration-dampening table, and an A/D converter (The Digidata 1440A digitizer, Molecular Device, Sunnyvale, Calif.). Acquired data are further filtered by an 8 pole low pass Bessel filter (LPF-8, Warner Instruments; Hamden, Conn.) at 1K Hz under a sampling frequency of 5 KHz. The software, pClamp 10.2 (Molecular Device, Sunnyvale, Calif.) and Origin Pro. 9.0 (OriginLab, Corp. Northampton, Mass.), are used to collect and process those data.

Results and Discussion

The planar lipid bilayer technique is extremely time-consuming, which stems from two embodiments of the experimental technique: the formation of a planar bilayer membrane on a small aperture and the fusion of protein-reconstituted liposomes into the planar bilayer membrane. These time-consuming problems are mitigated when the technique is used for some membrane ion channel proteins capable spontaneously insert into a planar bilayer since the proteins are not needed to form proteoliposomes to facilitate the protein fusion. Therefore, to speed up the protein insertion, a few research groups have focused on how to rapidly form planar bilayer membranes on the small aperture. However, for most membrane ion channel proteins, the planar bilayer membrane experiments could only be implemented after the proteins are successfully reconstituted into a liposome. Similarly, it has also been shown that direct incubation of the portal protein, GP10 with a well-formed planar bilayer membrane do not result in any protein insertion into the bilayer membrane. Hence, effectively controlling of the fusion of protein reconstituted vesicles into a well-formed planar bilayer membrane is key to speeding up the insertion of the portal proteins into the membrane, and thus depends upon the methods of preparing fusible proteoliposomes reconstituted with the portal proteins.

Figure 1B:
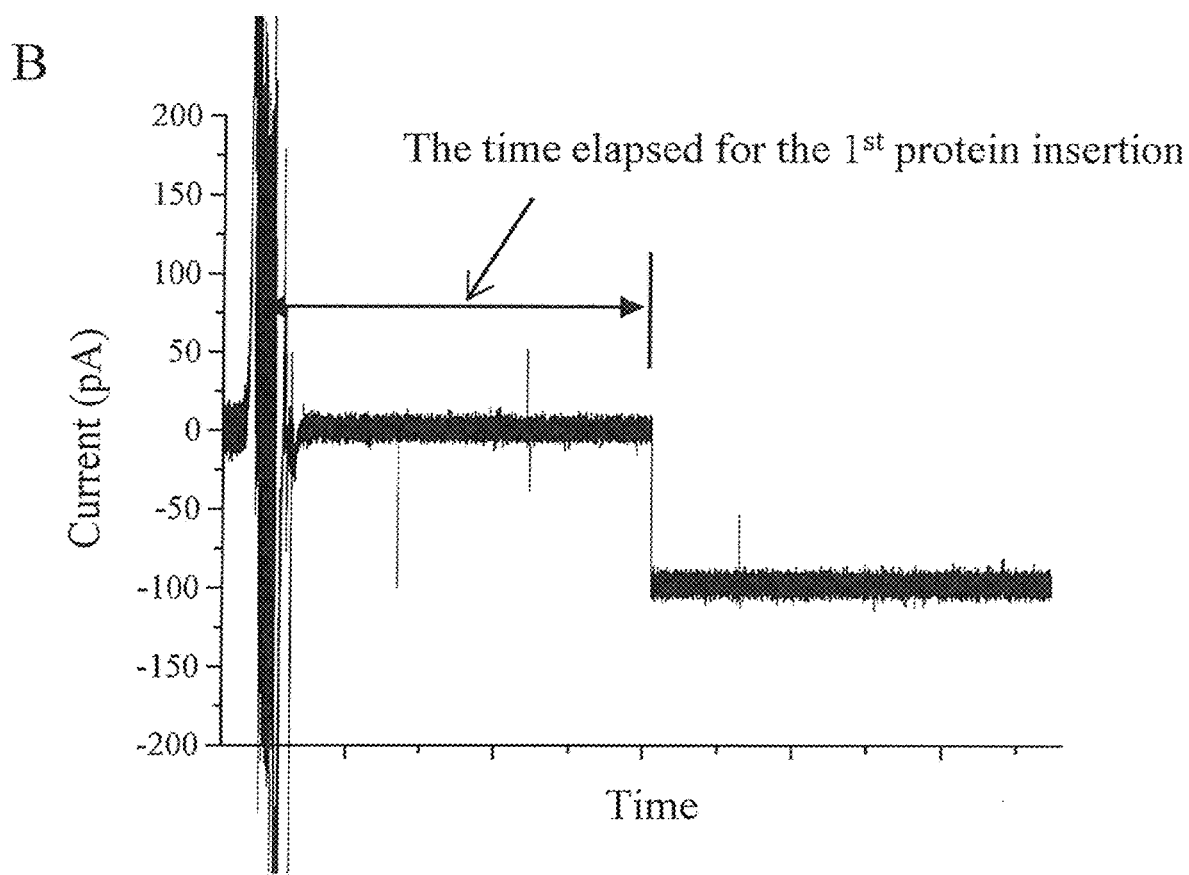
FIG. 1B is a typical record of current trace showing one portal channel inserted into a planar bilayer membrane after proteoliposomes were added to the cis-chamber.

In our experimental studies, the fusion of the proteoliposomes is kept under constant conditions throughout. FIG. 1A, demonstrates a schematic process for the fusion a single proteoliposome into a planar bilayer membrane. The formation of bilayer membranes can be monitored by a measurement of the membrane capacitance under a triangular voltage input. After the measured capacitance is found to be within the appropriate threshold range (80-100 pF), 1.0 μL of proteoliposome solution is added to the cis-compartment at the height of 5 mm farther from the top of a conducting buffer comprising 5 mM Tris (pH 8.0) with 1 M NaCl. As shown in FIG. 1B, the electric current is measured to be 0.0 pA before protein insertion occurred. When a single portal protein is inserted into a planar bilayer membrane by a fusion of a single proteoliposome, a stepwise current jump is recorded (FIG. 1B).

Figure 2:
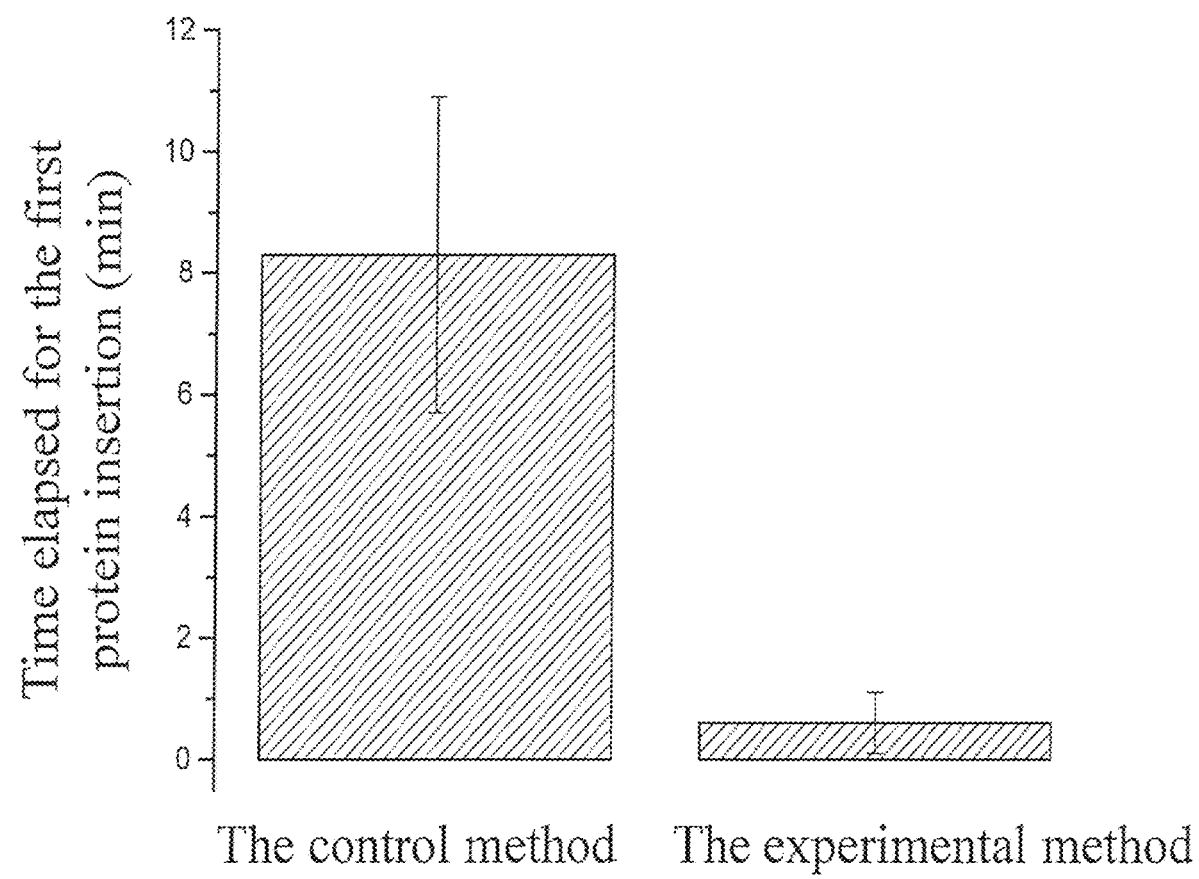
FIG. 2 shows the comparison of the time elapsed for the first insertion after the proteoliposomes prepared by the Conventional method and the novel Experimental Method disclosed herein were added to the BLM chambers.
Figure 9:
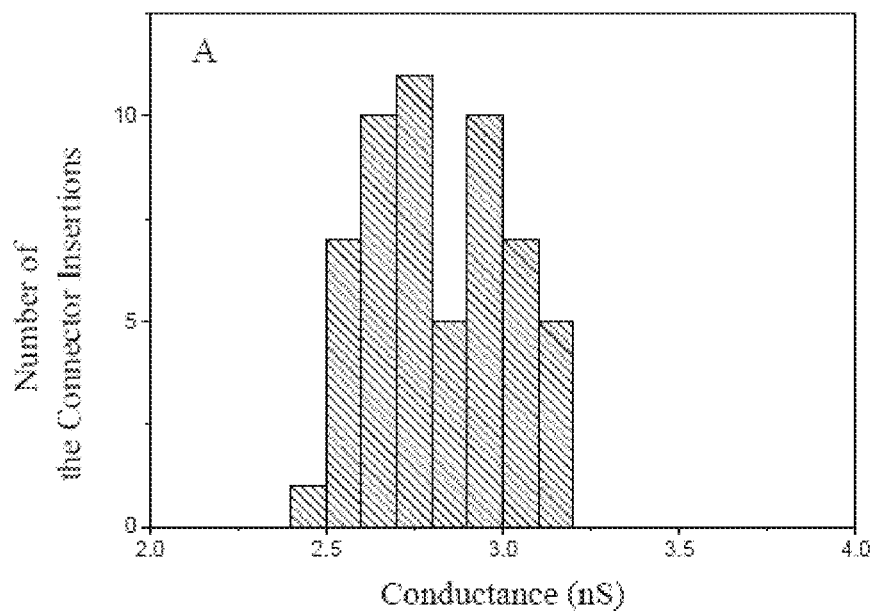
FIG. 9 is a histograms of the single-channel conductance measured on a pore formed by the C-His connector reconstituted liposomes prepared by the Experimental Method under an identical experimental conditions as the Conventional method shown in FIG. 10.
Figure 10:
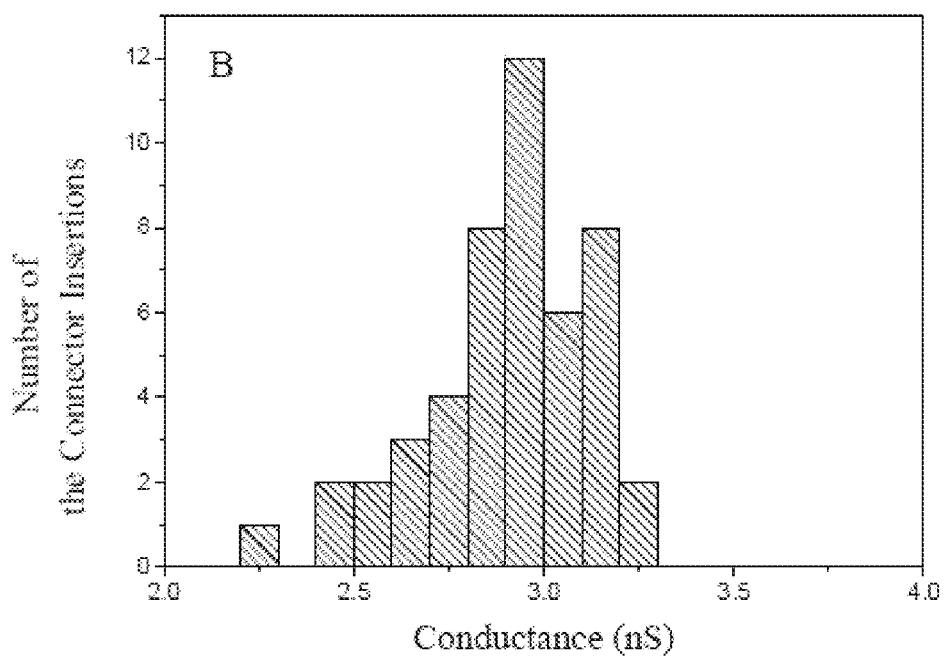
FIG. 10 is a histograms of the single-channel conductance measured on a pore formed by the C-His connector reconstituted liposomes prepared by the Conventional method under an identical experimental conditions as the Experimental Method shown in FIG. 9.

The single-channel conductances of the pores prepared by the Experimental and Conventional methods are compared in FIGS. 9 and 10. The statistical results have showed that the pores formed by the proteoliposomes from the Experimental Method have a distribution of the single-channel conductance similar to those formed by the proteoliposomes prepared by the Conventional Method under the identical experimental conditions, suggesting that proper folding of the connector protein is still maintained throughout the proteoliposome preparation using the Experimental Method. To identify which method produces more fusible proteoliposomes, the time elapsed is measured for the first insertion into independent lipid bilayer membranes as shown in FIG. 1B. The results from the proteoliposomes prepared by the two methods are shown in FIG. 2. The studies have demonstrated that an average of the time elapsed for the first insertion using the proteoliposomes prepared by the Conventional Method is 8.3±2.6 min (N=48). When the proteoliposomes prepared by the Experimental Method are used, the time elapsed for the first insertion is significantly decreased, an average of the time elapsed for the first insertion is measured to be 0.6±0.5 min (N=56), which suggests an average time reduction of 14-fold. The proteoliposomes prepared by the Experimental Method disclosed herein fuses more readily into the planar bilayer membranes than that prepared by Conventional Method.

A prior research has determined that the fusion rate of proteoliposomes into planar bilayer membranes is influenced mainly by two factors, the contact of the liposome vesicles with the planar bilayer membranes and the diffusion of the vesicles. Several reports have been published on the adjustments of the two factors to increase the proteoliposome fusion rate. These include: creation of osmotic gradient across the planar membrane with vesicle-containing side (cis-compartment) hyperosmotic with respect to the opposite (trans-compartment); induction of vesicle swelling by filling into the vesicles with hypertonic solution; the use of liposomes reconstituted with SNARE protein specializing in mediating intracellular fusion to catalyze the membrane fusion; the use of nystatin-induced liposomes; the use of cholesterol containing liposomes under low temperature; and the use of negatively charged lipid to prepare liposomes or the planar bilayer membrane in a $Ca^{2+}$ ion containing medium.

Compared with those reported methods, the Experimental Method disclosed herein is a more feasible and less complicated approach to prepare fusible proteoliposomes. To speed up the vesicle fusion rate, the new method simply replaced sucrose and the expensive surfactants with a high concentration of glycerol. As shown in FIG. 2, the presence of the high concentration of glycerol (>20% (V/V)) resulted in an increase in the osmotic pressure and the density of the prepared liposomes. In the Experimental Method, the molarity of glycerol inside the proteoliposomes is at least 2700 mM, about 13.5 fold greater than the molarity of sucrose (200 mM) used in the preparation of proteoliposomes by Conventional Method. As a result, the swelling rate for vesicles in contact with planar bilayer membrane increased. Furthermore, the density of glycerol also played an important role. The 20% (V/V) of glycerol in a water solution at room temperature has a density of more than 1.05 g/mL and 200 mM sucrose has a density of 1.02 g/mL. The density difference would be more favorable for the glycerol-based liposomes in a horizontal bilayer lipid membrane (BLM) chamber to move towards the bilayer membranes under gravitational force in a high-salt conducting buffer, resulting in more vesicles in contact with the membrane within a shorter time. To further understand and rationalize this discovery, another independent experiment is carried out. The horizontal chamber is replaced with a vertical BLM chamber to perform the planar bilayer membrane insertion experiment using the proteoliposomes prepared by the new Experimental Method. Because a 200-um aperture is located on the sidewall of the vertical chamber, after the proteoliposomes are added to the aperture of the chamber, most of the high-density proteoliposomes settled on the bottom of the chamber under the gravitational force. Under mechanical stirring, only one out of 36 independent bilayer membranes showed that a protein insertion has happened. The results indicates that the proteoliposomes prepared by the Experimental Method are more appropriate for the planar lipid bilayer experiments when a horizontal BLM chamber is used.

It should be noted that the use of more than 200 mM sucrose to prepare the liposomes in the Conventional Method would also result in an increase in the density and osmotic pressure of the formed proteoliposomes. However, unlike the Experimental Method where glycerol is used, such an increase, is limited by the solubility of sucrose in the buffer used. For example, a maximum concentration of 300 mM of sucrose was reported to be used to prepare the proteoliposomes reconstituted with a membrane channel protein, voltage-gated K channel KAT1 or the mutant portal protein, GP10.

The planar lipid bilayer membrane technique has been proved be an effective method for the determination of physical dimension of pores formed by some ion channel proteins. The measurement is particularly useful to the approximation of the channel size of the proteins whose crystal data are not available yet. In the size approximation measurement, nonelectrolytes including glycerol as well as PEG with different molecular weights, are typically mixed with a conducting buffer containing KCl salt. Measurements of the protein channel conductance are dependent upon the size of the nonelectrolytes. Polymers, e.g., PEG, which are sufficiently small to enter the channel's pore, will decrease the channel's conductance. Polymers with radii larger than those of the two pore entrances rarely partition into the pore, and thus will not affect the channel conductance. On the other hand, nonelectrolytes always decrease the bulk conductivity of a conducting buffer. As a result, the dependence of the channel conductance on the polymer molecular mass can be used to deduce the pore's radius using a mathematical relationship between the measured channel conductance and the conductivity of the bulk conducting buffer solutions used. To date, the method has been successfully applied for *Borrelia burgdorferi* $P_{13}$ Porin and $P_{66}$ Porin, Colicin Ia channels, *Bacillus anthracis* $PA_{63}$ channels, Engineered FhuA Δc/Δ4L Protein, epsilon toxin, *staphylococcal* α-toxin as well as to cholera toxin channels (O. V. Krasilnikov, et al., *FEMS Microbiol. Lett.*, 1992, 105, 93).

Nonetheless, those size measurements have seldom been used for channel proteins that require forming proteoliposomes to facilitate the protein fusion into planar bilayer membranes. One reason might be attributed to the difficulty in the fusion of the proteoliposomes into the bilayer membranes in a buffer solution containing nonelectrolytes, such as glycerol or PEG. When a conducting buffer is mixed with a high concentration of nonelectrolytes, the density and the viscosity of the buffers are increased, which would significantly slow down the rate for the fusion of the proteoliposomes into the bilayer membrane. For example, when the GP10 proteoliposomes prepared by the Conventional Method is added to a BLM chamber bathed in a 1M KCl, 5 mM HEPES (pH 7.4) containing 20% glycerol, no GP10 connector protein insertion can be found.

Figure 3:
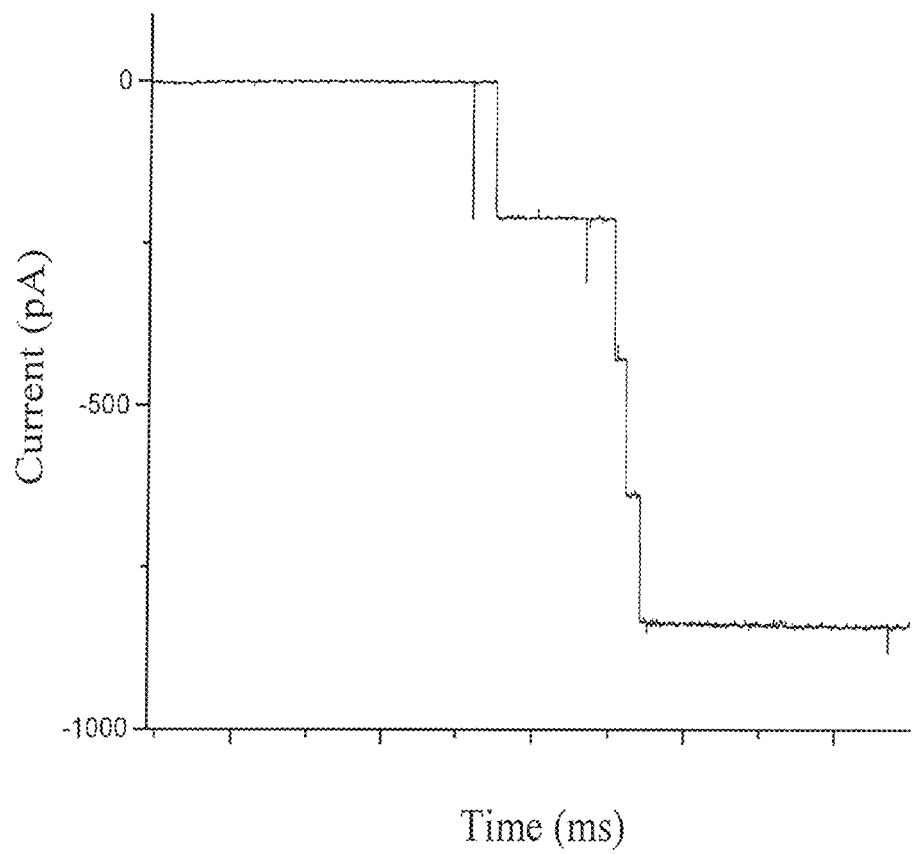
FIG. 3 is the current record showing continuous C-His GP10 connector insertion into a planar bilayer membrane in a 1 M KCl (pH 7.4 5 mM 2-(4-(2-hydroxyethyl)-1-piperazinyl) ethane sulfonic acid (HEPES) buffer containing 20% glycerol (V/V) solution)
Figure 6:
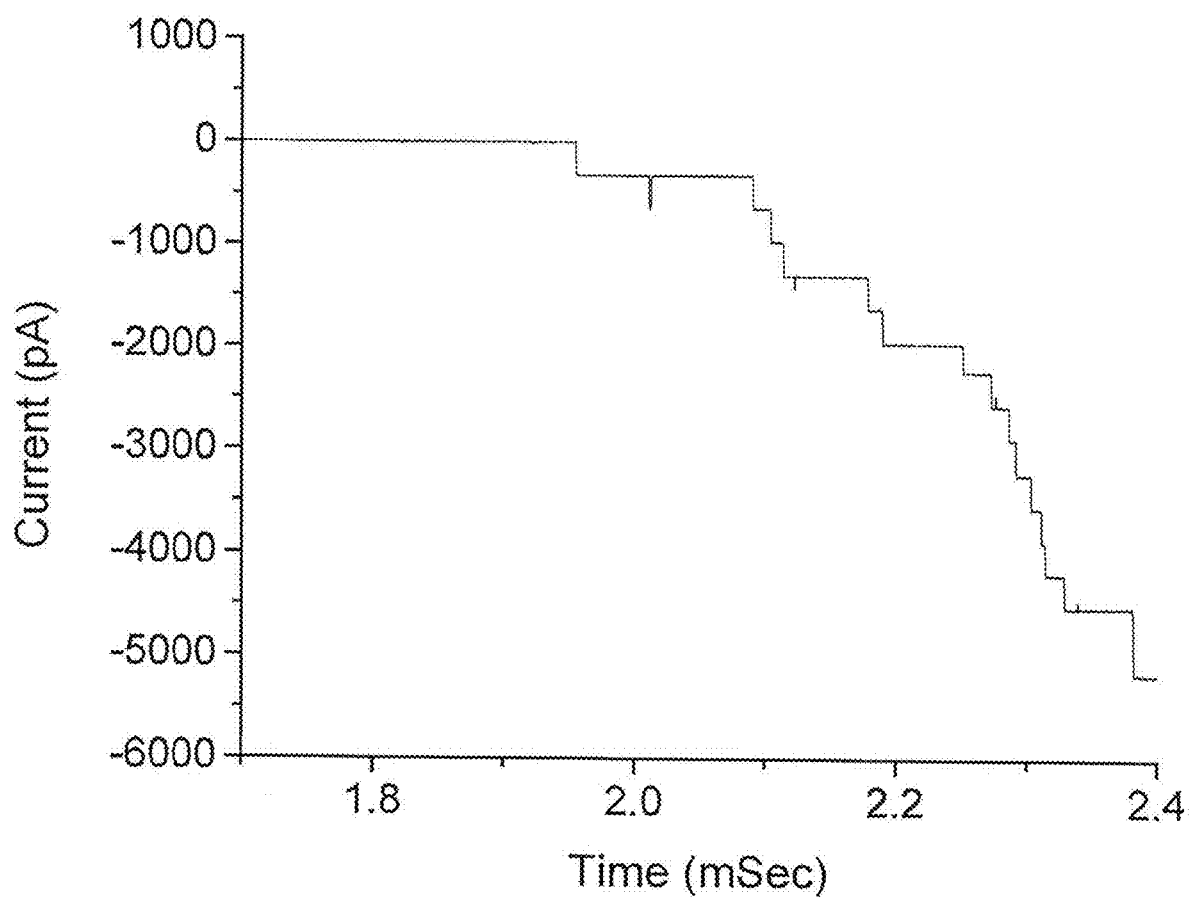
FIG. 6 shows the measured current of C-His GP10 insertion into a planar bilayer membrane using proteoliposomes prepared with Polyethylene glycols (PEG) (MW 3350 Da) (Measurement conditions: @-75 mV, the bilayer bathed in a 1 M KCl (pH 7.4) mixed with PEG (MW 8000 Da))

Development of a method to prepare fusible proteoliposomes in the conducting buffers containing nonelectrolytes is of particular significance to the structural studies on the phage portal proteins because the crystal data of most phage portal proteins are currently unavailable. The proposed method in this paper provided a possible solution. Considering that the density and viscosity are significantly increased in the conducting buffer containing 20% (V/V) glycerol, a rehydration buffer, 1 M KCl, 5 mM HEPES (pH 7.4) with 25% glycerol (V/V), is used to prepare the GP10 proteoliposomes for the planar bilayer experiments as shown in FIG. 3. It was found that there were still a constant of supply of vesicles in the viscous buffer and steady rates of fusions are also observed (FIG. 3). To test how the channel conductance is affected by the size of nonelectrolytes used, the proteoliposomes are used to measure the single channel conductance of GP10 in the buffer containing PEG (MW: 8000). FIG. 6 shows the measured current of C-His GP10 insertion into a planar bilayer membrane using proteoliposomes prepared with PEG (MW 3350Da) (Measurement conditions: @-75 mV, the bilayer bathed in a 1 M KCl (pH 7.4) mixed with PEG).

A summary of those results is shown in Table 1. The average conductance of single connector channel is measured to be 2.81±0.09 nS (N=41) in the presence of 20% glycerol vs 4.46±0.12 nS (N=52) in the absence of glycerol. The decrease in the single channel conductance is a result of the occupancy by the non-conducting glycerol molecules in the channel of the GP10 connector. However when 20% PEG (MW: 8000) is used, the conductance measured is 4.28±0.15 nS (N=65), close to 4.46±0.12 nS (N=52) in the buffer without the PEG, which indicated that the polymer molecules are excluded by the channel of the GP10 connector channel due to its bulky size. Those results demonstrated that the Experimental Method is a highly effective method in the preparation of fusible proteoliposomes for the use in buffers containing nonelectrolytes.

TABLE 1

Measurement of Single Channel Conductance of GP10 Connector in different conducting buffers

| Conducting Buffer | Conductance (nS) |
|---|---|
| 1M KCl (5.0 mM HEPES pH 7.4) | 4.46 ± 0.12 (N = 52) |
| 1M KCl (5.0 mM HEPES pH 7.4) with 20% PEG (MW: 8000) | 4.28 ± 0.15 (N = 65) |
| 1M KCl (5.0 mM HEPES pH 7.4) with 20% glycerol | 2.81 ± 0.09 (N = 4 |

The Conventional Method was the first reported technique to prepare fusible vesicles reconstituted with a mutant phage portal protein, GP10 connector, for the planar bilayer membrane experiments (D. Wendell, et al., *Nat. Nanotechnol.* 2009, 4, 765). In those conventional dehydration-rehydration methods, an appropriate amount of surfactants is typically added to rehydration buffers to help to increase the solubility of hydrophobic channel proteins when they are in contact with the lipid molecules during the rehydration step. Proteoliposomes are typically formed by means of a time-consuming step for surfactant removal using reagents, such as Biobeads. Though the Conventional Method takes less time at this step, the protein self-aggregation becomes a big issue during the rehydration step. Consequently, it was found that several mutant GP10 portal proteins, for example, N-His tagged connector, self-aggregated during the rehydration step when the Conventional Method is used.

To explore whether the new Experimental Method disclosed herein may be used to for more hydrophobic portal proteins, the method is used to prepare proteoliposomes with a purified mutant portal protein, GP20 (20amN50

Figure 4A:
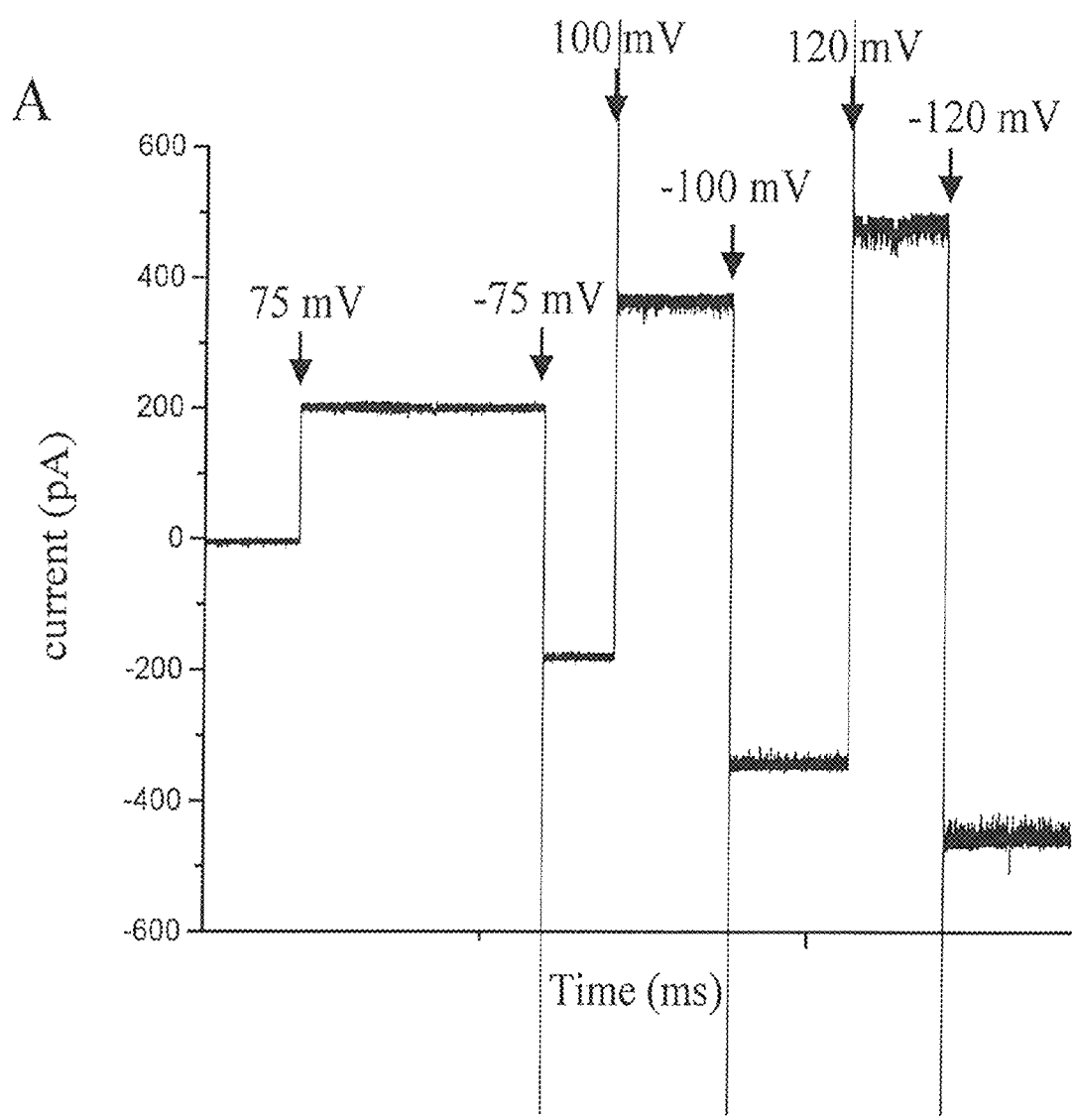
FIG. 4A shows the current of a single insertion of the mutant portal protein, GP20 (20amN50(Q325am)), from bacteriophage T4 in a planar bilayer membrane under various voltages.
Figure 4B:
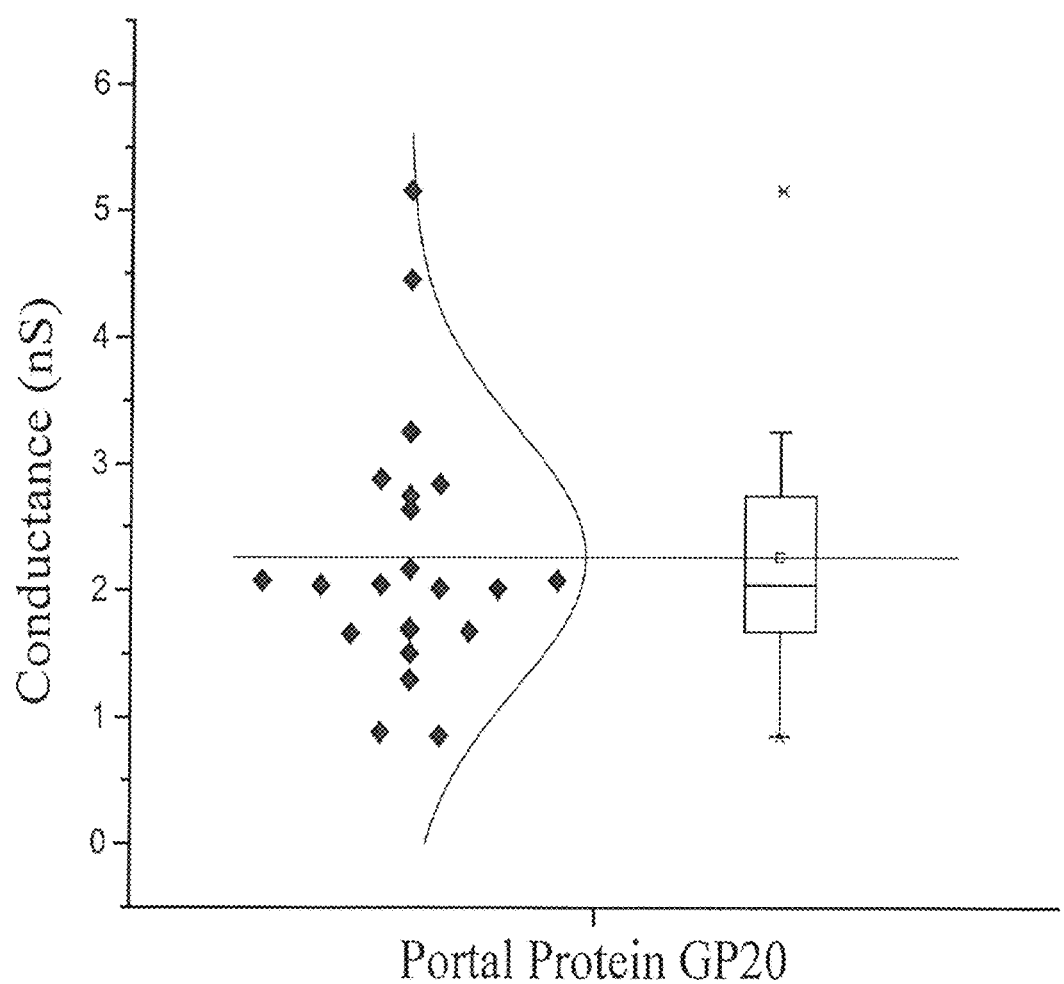
FIG. 4B is a Box Plot showing a distribution of measurements for single channel conductance of GP20 (20amN50 (Q325am)) under -75mV in 1 M NaCl buffer (5 mM Tris pH 8.0)
Figure 5:
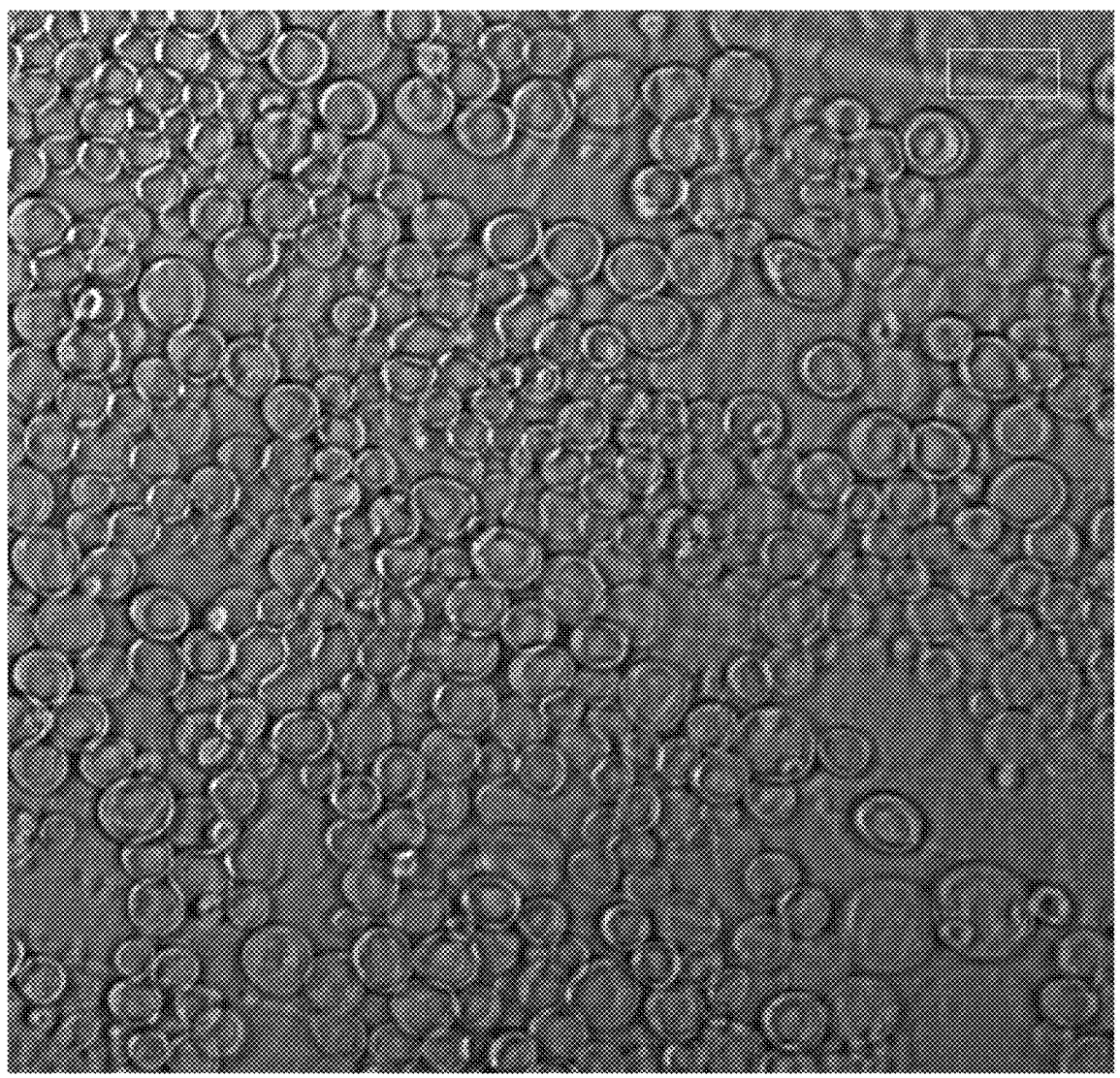
FIG. 5 shows the image of prepared proteoliposomes reconstituted with C-His GP10 using the recipe in the Experimental Method.

(Q325am)), from bacteriophage T4 (V. Padilla-Sanchez, et al. *J. Mol. Biol.* 2014, 426, 1019). The portal protein is structurally well-conserved and also forms the dodecameric portal channel through which DNA enters during packaging and exists during infection. During assembly of T4 protein, the portal protein needs to be bound to cell membrane to initiate the scaffolding core assembly. GP20 is highly hydrophobic and thus has a limited aqueous solubility. The proteoliposomes prepared by the new Experimental Method are added to 1 M NaCl 5 mM Tris (pH 8.0) buffer and the results are shown in FIG. 4A. A current jump indicating an insertion of a single GP20 protein molecule is recorded. Under the voltages applied, the portal channels are kept open under the experimental conditions. The distribution of the conductance of a single channel of the mutant GP20 is shown in FIG. 4B. The average conductance for the mutant GP20 is 2.25±1.03 nS (N=23), lower than the average of the single channel conductance, 3.04±0.56 nS, from C-His GP10 in the same buffer reported previously (P. Jing, et al., *Mol. BioSyst.* 2010, 6, 1844). Although the crystal data of the mutant GP20 is currently unavailable due to its high hydrophobicity and low solubility, the results of measured conductance suggest that the size of the mutant GP20 channel should be 26% smaller than that of C-His GP10, which is consistent with the results of a recently published paper (L. Sun, et al., *Nature Communications,* 2015, 6, 1-11). The result disclosed herein is the first evidence that portal protein GP20 from bacteriophage T4 can be functionally inserted into a planar bilayer membrane. Those data indicate that the planar lipid bilayer membrane technique may be an important new tool for researchers to perform structural-function study on the roles that GP20 protein plays in the head assembly, genome packaging, neck/tail attachment and genome ejection in Bacteriophage T4. The results also suggest that although all the phage portal proteins are structurally conserved, due to little sequence identity among the portal proteins, the size and channel properties of the portal proteins vary significantly among different bacteriophages. Therefore the large family of the underexplored portal proteins from bacteriophages and herpesvirus would provide more options in choosing an appropriate biological pore as a sensing motif for the single-molecule nanopore technology. FIG. 5 shows the image of the giant proteoliposomes reconstituted with C-His GP10 protein using the method disclosed herein.

The successful insertion of the mutant GP20 into the planar bilayer membranes in FIG. 4B is a consequence of the use of higher concentration of glycerol to prepare the proteoliposomes in the Experimental Method. It is also successfully used to insert hydrophobic mutant GP10 connectors, e.g., N-His GP10, into a lipid bilayer membrane. The connector protein is not denaturized due to that the distribution of the single-channel conductance of the protein pores in the bilayer membranes is not affected, as shown in FIGS. 9 and 10.

Glycerol used in the new Experimental Method disclosed herein improves the solubility of the hydrophobic portal proteins during the rehydration step, which is similar to the roles that the surfactants play in the rehydration step for the conventional hydration-dehydration methods. Overall Experimental Method disclosed herein is a faster proteoliposome preparation method since it does not need to remove the glycerol and thus can avoid the time-consuming step for surfactant removal used in the conventional hydration-dehydration process.

Figure 7:
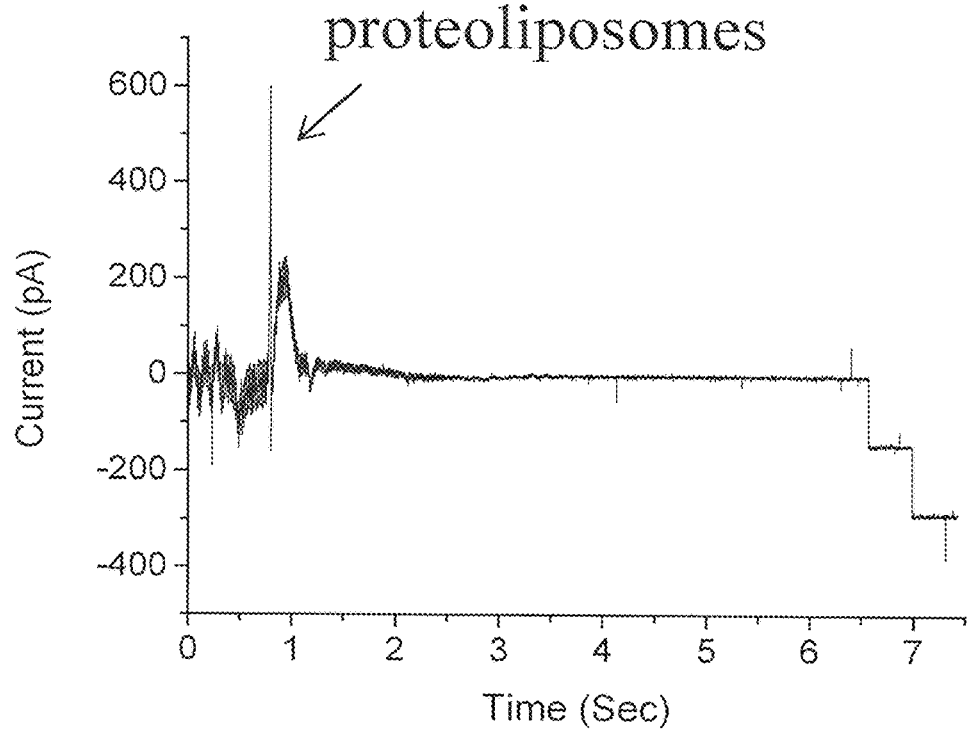
FIG. 7 shows the insertions of C-His connectors using a batch of proteoliposome that has been stored at −80° C. for 3 years (Measurement conditions: @-60 mV the bilayer membrane bathed in a 1 M NaCl buffer (pH 7.8))
Figure 8:
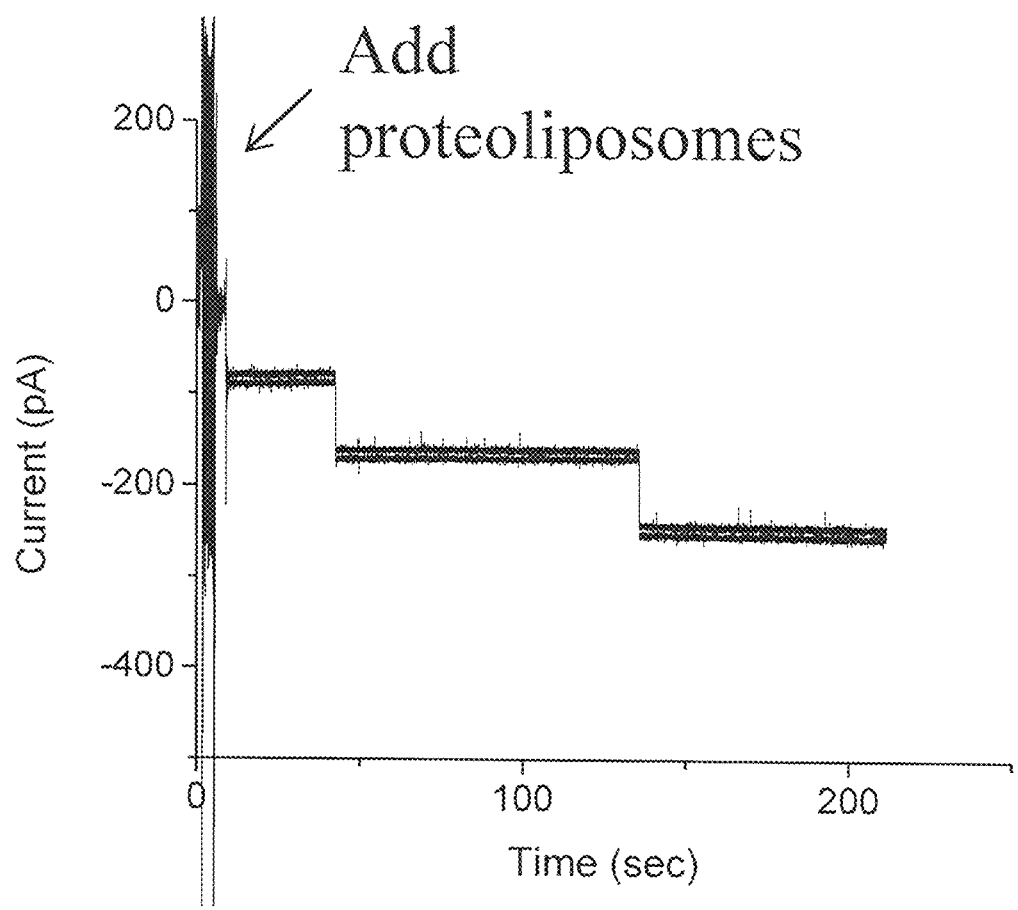
FIG. 8 shows the insertions of C-His connectors using a batch of proteoliposomes that has been stored at 4° C. for 6 months (Measurement conditions: @-40 mV, the bilayer membrane bathed in a 1 M NaCl buffer (pH 7.8))

Finally, it is discovered that the shelf life of proteoliposomes prepared by the new Experimental Method has been significantly improved, which is more than 2 years at −80° C. or 3-4 months at 4° C., longer than that of those prepared using the conventional dehydration-rehydration methods. The reported shelf life of the proteoliposomes prepared by Conventional Method is less than 6 months at −80° C. or about 1-2 weeks at 4° C. FIG. 7 shows the insertion of C-His connector protein using a batch of proteoliposomes that has been stored at −80° C. for 3 years in our laboratory (Measurement conditions: @−60 mV the bilayer membraned bathed in 1 M NaCl buffer (pH 7.8)). FIG. 8 shows the insertions of C-His connectors using a batch of proteoliposomes that has been stored at 4° C. for 6 months (Measurement conditions: @−40 mV, the bilayer membraned bathed in a 1 M NaCl buffer (pH 7.8)).

The extended shelf life results suggested that the proteoliposomes prepared by the new Experimental Method disclosed herein can be transported and shared more conveniently between research labs, which would also be of greater value to future commercialization of the proteoliposomes for different biomedical applications.

In summary, a new method to prepare proteoliposome is disclosed, which offers at least four advantages over the conventional dehydration-rehydration method. The first improvement lay in changing from glycerol to replace sucrose, which imparted the stability of proteins and prevention of proteins from aggregation. Second, the density and osmotic pressure of the formed proteoliposomes could be adjusted by the use of different concentrations of glycerol in the rehydration step, which would control the rate for the contact of the proteoliposomes with the planar bilayer membranes and the subsequent proteoliposome fusion into the membrane when different buffers were used. The insertion of phage portal proteins is fast, controllable and predictable in horizontal BLM chambers. Experiments have confirmed that the average time elapsed for the first portal protein insertion is decreased by 14 fold to less than 1 min. The third benefit of the new method disclosed herein is the much increased stability of the formed liposomes owing to the existence of glycerol. Storage and transport of liposomes would become more convenient. The feature is useful when the proteoliposomes are commercialized for different biomedical applications. Finally, the method is practical and simple to perform. It does not need a specially made lipid molecule or an engineered portal protein to facilitate the portal protein insertion. Therefore, the method disclosed herein provides a rapid, simple and practical approach prepare proteoliposomes and the downstream application on a planar lipid bilayer membrane. The technical advance will have a significant impact on the research areas of nanotechnology, biophysics, and microbiology.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A planar lipid bilayer membrane comprising a single viral portal protein molecule manufactured according to the steps of:
   a) preparing a lipid solution in an organic solvent;
   b) preparing a viral portal protein solution;
   c) combining said lipid solution and said viral portal protein solution in a flask;
   d) removing said organic solvent from the combined solution from step c), under vacuum with constant mixing, to afford a residue;
   e) adding an aqueous buffer to the residue of step d), wherein said aqueous buffer is doped with glycerol or a polyethylene glycol (PEG);
   f) rehydrating the mixture of step e) by gentle agitation;
   g) extruding the rehydrated mixture of step f) through a polycarbonate membrane, wherein the polycarbonate membrane has a pore size ranging from about 50 nm to about 400 nm; and
   h) repeating step g) for about five to fifty times to afford said planar lipid bilayer membrane comprising a single viral portal protein molecule.

2. A device incorporated the planar lipid bilayer membrane comprising a single channel viral portal protein molecule.

3. A planar lipid bilayer membrane comprising a single viral portal protein molecule, wherein said single viral portal protein molecule is derived from a proteoliposome manufactured according to the steps of:
   a) preparing a lipid solution in an organic solvent;
   b) preparing a viral portal protein solution;
   c) combining said lipid solution and said viral portal protein solution in a flask;
   d) removing said organic solvent from the combined solution from step c), under vacuum with constant mixing, to afford a residue;
   e) adding an aqueous buffer to the residue of step d), wherein said aqueous buffer is doped with glycerol or a polyethylene glycol (PEG);
   f) rehydrating the mixture of step e) by gentle agitation;
   g) extruding the rehydrated mixture of step f) through a polycarbonate membrane, wherein the polycarbonate membrane has a pore size ranging from about 50 nm to about 400 nm; and
   h) repeating step g) for about five to fifty times to afford said proteoliposome.

4. The planar lipid bilayer membrane comprising a single viral portal protein molecule of claim 3, wherein said protein is selected from the group consisting of a mutant portal protein C-His GP10 from bacteriophage Phi29, and a mutant portal protein GP20 (20amN50(Q325am)) from bacteriophage T4.

5. The planar lipid bilayer membrane comprising a single viral portal protein molecule of claim 3, wherein the concentration of said glycerol ranges from about 1% to about 99% (v/v).

6. The planar lipid bilayer membrane comprising a single viral portal protein molecule of claim 3, wherein said polyethylene glycols (PEG) concentration ranges from about 0.1% to about 60% (v/v).

7. The planar lipid bilayer membrane comprising a single viral portal protein molecule of claim 3, wherein the molecular weight of said polyethylene glycols (PEG) ranges from about 200 Da to about 8,000 Da.

8. The planar lipid bilayer membrane comprising a single viral portal protein molecule of claim 3, wherein said lipid is 1,2-diphytanoyl-sn-glycero-3 phosphocholine (DPhPC), diacetyl phosphatidylcholine (DAcPC), 1,2-dioleoyl-sn-glycero-3-phosphocholine (DOPC), or the like.

9. A device incorporated the planar lipid bilayer membrane comprising a single viral portal protein molecule according to claim 3.

* * * * *